(12) United States Patent
Koseoglu et al.

(10) Patent No.: US 10,725,013 B2
(45) Date of Patent: Jul. 28, 2020

(54) CHARACTERIZATION OF CRUDE OIL BY FOURIER TRANSFORM ION CYCLOTRON RESONANCE MASS SPECTROMETRY

(71) Applicant: Saudi Arabian Oil Company

(72) Inventors: Omer Refa Koseoglu, Dhahran (SA); Adnan Al-Hajji, Dhahran (SA); Hendrik Muller, Dhahran (SA); Hanadi H. Jawad, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 347 days.

(21) Appl. No.: 15/639,522

(22) Filed: Jun. 30, 2017

(65) Prior Publication Data
US 2017/0363602 A1  Dec. 21, 2017

Related U.S. Application Data

(63) Continuation-in-part of application No. 13/467,693, filed on May 9, 2012, now abandoned, and a
(Continued)

(51) Int. Cl.
*G01N 31/00* (2006.01)
*G01N 33/28* (2006.01)
(Continued)

(52) U.S. Cl.
CPC ..... *G01N 33/2823* (2013.01); *G01N 33/2811* (2013.01); *G01N 33/2829* (2013.01);
(Continued)

(58) Field of Classification Search
CPC ........... G01N 33/2823; G01N 33/2811; G01N 33/2829; G16C 20/23; H01J 49/0036
(Continued)

(56) References Cited

U.S. PATENT DOCUMENTS 3,617,501 A  11/1971  Eng
3,896,312 A   7/1975  Brown
(Continued)

FOREIGN PATENT DOCUMENTS

CA  2781273 A1  12/2013
EP  0305090 A2   8/1988
(Continued)

OTHER PUBLICATIONS

Adhvaryu, A. et al., Quantitative NMR Spectroscopy for the Prediction of Base Oil Properties, Tribology Transactions, vol. 43, No. 2, 2000, pp. 245-250.
(Continued)

*Primary Examiner* — Michael P Nghiem
(74) *Attorney, Agent, or Firm* — Abelman, Frayne and Schwab

(57) ABSTRACT

A system, method and computer program product are provided for calculating one or more indicative properties including one or more of the cetane number, octane number, pour point, cloud point and aniline point of oil fractions, from the density and Fourier transform ion cyclotron resonance mass spectrometry (FT-ICR MS) of a sample of an oil sample.

14 Claims, 4 Drawing Sheets

Related U.S. Application Data continuation-in-part of application No. PCT/US2016/012147, filed on Jan. 5, 2016.

(60) Provisional application No. 61/502,385, filed on Jun. 29, 2011, provisional application No. 62/099,743, filed on Jan. 5, 2015.

(51) Int. Cl.
    *H01J 49/00* (2006.01)
    *G16C 20/30* (2019.01)
    *H01J 49/38* (2006.01)

(52) U.S. Cl.
    CPC .......... *G16C 20/30* (2019.02); *H01J 49/0036* (2013.01); *H01J 49/38* (2013.01)

(58) Field of Classification Search
    USPC ...................................................... 702/25
    See application file for complete search history.

(56) References Cited

U.S. PATENT DOCUMENTS

| | | |
|---|---|---|
| 4,251,870 A | 2/1981 | Jaffe |
| 4,897,177 A | 1/1990 | Nadler |
| 4,971,915 A | 11/1990 | Schwartz et al. |
| 4,988,446 A | 1/1991 | Haberman |
| 5,121,337 A | 6/1992 | Brown |
| 5,223,714 A | 6/1993 | Maggard |
| 5,266,800 A | 11/1993 | Mullins |
| 5,304,807 A | 4/1994 | Lin |
| 5,424,959 A | 6/1995 | Reyes |
| 5,452,232 A | 9/1995 | Espinosa et al. |
| 5,475,612 A | 12/1995 | Espinosa |
| 5,490,085 A | 2/1996 | Lambert et al. |
| 5,572,030 A | 11/1996 | Ranson et al. |
| 5,600,134 A | 2/1997 | Ashe et al. |
| 5,602,755 A | 2/1997 | Ashe et al. |
| 5,656,810 A | 8/1997 | Alfano et al. |
| 5,699,269 A | 12/1997 | Ashe et al. |
| 5,699,270 A | 12/1997 | Ashe et al. |
| 6,070,128 A | 5/2000 | Descales |
| 6,258,987 B1 | 7/2001 | Schmidt et al. |
| 6,275,775 B1 | 8/2001 | Baco |
| 6,490,029 B1 | 12/2002 | Cho |
| 6,602,403 B1 | 8/2003 | Steffens et al. |
| 6,611,735 B1 | 8/2003 | Henly |
| 6,633,043 B2 | 10/2003 | Hegazi |
| 6,662,116 B2 | 12/2003 | Brown |
| 6,711,532 B1 | 3/2004 | Spieksma |
| 6,841,779 B1 | 1/2005 | Roehner et al. |
| 6,893,874 B2 | 5/2005 | Stark |
| 7,126,332 B2 | 10/2006 | Blanz |
| 7,173,239 B2 | 2/2007 | DiFoggio |
| 7,560,711 B2 | 7/2009 | Hegazi |
| 7,598,487 B2 | 10/2009 | Qian |
| 8,714,246 B2 | 5/2014 | Pop et al. |
| 8,930,149 B1 | 1/2015 | Koseoglu et al. |
| 9,285,307 B2 | 3/2016 | Koseoglu et al. |
| 9,423,391 B2 | 8/2016 | Koseoglu et al. |
| 9,429,556 B2 | 8/2016 | Koseoglu et al. |
| 9,778,240 B2 | 10/2017 | Koseoglu et al. |
| 9,816,919 B2 | 11/2017 | Koseoglu et al. |
| 2002/0052769 A1 | 5/2002 | Navani et al. |
| 2003/0042414 A1* | 3/2003 | Smith ............... H01J 49/0009 250/282 |
| 2003/0141459 A1 | 7/2003 | Hegazi et al. |
| 2003/0195708 A1 | 10/2003 | Brown |
| 2005/0109934 A1 | 5/2005 | David |
| 2005/0173298 A1 | 8/2005 | Wellington |
| 2006/0043004 A1 | 3/2006 | Rose |
| 2006/0047444 A1 | 3/2006 | Brown |
| 2006/0142955 A1 | 6/2006 | Jones |
| 2007/0050154 A1 | 3/2007 | Albahri |
| 2007/0231912 A1 | 10/2007 | Reischman et al. |
| 2007/0295640 A1 | 12/2007 | Tan et al. |
| 2008/0037006 A1 | 2/2008 | Canas Triana |
| 2008/0040051 A1 | 2/2008 | Franklin et al. |
| 2008/0206887 A1 | 8/2008 | Chen |
| 2008/0248967 A1 | 10/2008 | Butler et al. |
| 2008/0253426 A1 | 10/2008 | Voelkening |
| 2008/0260584 A1 | 10/2008 | Gudde et al. |
| 2009/0011517 A1 | 1/2009 | Hodges |
| 2009/0180949 A1 | 7/2009 | Cui |
| 2009/0279072 A1 | 11/2009 | Arakawa |
| 2009/0290144 A1 | 11/2009 | Hegazi |
| 2009/0316139 A1 | 12/2009 | Shrestha |
| 2010/0049681 A1 | 2/2010 | Pradhan |
| 2010/0113311 A1 | 5/2010 | Eccleston et al. |
| 2010/0204925 A1 | 8/2010 | Albahri |
| 2010/0211329 A1 | 8/2010 | Farquharson et al. |
| 2010/0218585 A1 | 9/2010 | Chawla |
| 2011/0152136 A1 | 6/2011 | Hughes et al. |
| 2011/0240841 A1* | 10/2011 | Lange ............... H01J 49/0036 250/282 |
| 2011/0308996 A1 | 12/2011 | Choudhary |
| 2012/0171151 A1 | 7/2012 | Thomassian |
| 2013/0013274 A1* | 1/2013 | Grothe, Jr. ........ H01J 49/0036 703/2 |
| 2014/0075827 A1 | 3/2014 | Gonzalez et al. |
| 2014/0156241 A1 | 6/2014 | Kumar et al. |
| 2015/0106027 A1 | 4/2015 | Koseoglu et al. |
| 2015/0106028 A1* | 4/2015 | Koseoglu ............... G16C 20/30 702/23 |
| 2015/0106029 A1 | 4/2015 | Koseoglu et al. |
| 2015/0106031 A1 | 4/2015 | Koseoglu et al. |
| 2015/0112610 A1 | 4/2015 | Koseoglu |
| 2015/0112611 A1 | 4/2015 | Koseoglu |
| 2016/0011102 A1 | 1/2016 | Koseoglu et al. |
| 2016/0187253 A1 | 6/2016 | Koseoglu et al. |
| 2016/0195481 A1 | 7/2016 | Koseoglu |
| 2016/0195507 A1 | 7/2016 | Koseoglu |
| 2016/0195508 A1 | 7/2016 | Al-Hajji |
| 2016/0377589 A1 | 12/2016 | Koseoglu |
| 2017/0003217 A1 | 1/2017 | Koseoglu |
| 2017/0363540 A1 | 12/2017 | Koseoglu |
| 2017/0363591 A1 | 12/2017 | Koseoglu |
| 2017/0363602 A1 | 12/2017 | Koseoglu |
| 2017/0363603 A1 | 12/2017 | Koseoglu |

FOREIGN PATENT DOCUMENTS

| | | |
|---|---|---|
| EP | 0304232 A2 | 2/1989 |
| EP | 0552300 A1 | 7/1993 |
| EP | 0794433 A1 | 9/1997 |
| EP | 0859236 A1 | 8/1998 |
| EP | 0984277 A1 | 3/2000 |
| SU | 817486 A1 | 3/1981 |
| SU | 1523972 A1 | 11/1989 |
| WO | 03/048759 A1 | 6/2003 |
| WO | 2004033513 A2 | 4/2004 |
| WO | 2006030218 A1 | 3/2006 |
| WO | 2009082418 A2 | 7/2009 |
| WO | 2013102916 A1 | 7/2013 |
| WO | WO-2016111988 A1 * | 7/2016 ......... G01N 33/2823 |

OTHER PUBLICATIONS

Albahri, T. et al, Octane Number And Aniline Point of Petroleum Fuels, 2002, Fuel Chemistry Division, vol. 47(2), pp. 710-711.

Ali, M., Resolution and Quantification of Ring Type Aromatics by HPLC Method using N-Hexane Elution, 2003, King Fahd University of Petroleum and Minerals, pp. 1-9.

ASTM D2887-01, Standard Test Method for Boiling Range Distribution of Petroleum Fractions by Gas Chromatography, Annual Book of ASTM Standards, vol. 14, No. 02, pp. 204-216, 2001.

Birch C., Oil & Gas Journal, Jan. 14, 2002, pp. 54-59 (printed Jul. 9, 2014 from http://www.ogj.com/articles/print/volume-100/issue-2/processing/achieving-maximum-crude-oil-value-depends-on-accurate-evaluation.html).

(56) References Cited

OTHER PUBLICATIONS

Bowden, J. et al., Octane-Cetane Relationship, 1974, NTIS, p. 8.
Chemstations, Inc, Physical Properties User's Guide, 2004, Chemstations Inc., Ver. 5.4, pp. 18-22.
Cookson, D.J. et al., Investigation of the Chemical Basis of Diesel Fuel Properties, Energy & Fuels, vol. 2, No. 6, 1988, pp. 854-860.
Duvekot, C., Fast Analysis of Paraffins, iso-Paraffins, Olefins, iso-Olefins, Naphthenes and Aromatics in Hydrocarbon Streams, Varian, Inc, 2008, pp. 1-4.
Evokimov, I, et al, Potential of UV-Visible Absorption Spectroscopy for characterizing Crude Petroleum Oils, Oil an Gas Business, 2007, 21 pages.
Falla, F, et al., Characterization of crude petroleum by NIR, Journal of Petroleum Science and Engineering, vol. 51, 2006, pp. 127-137.
Fernandez-Lima, F. et al., Petroleum Crude Oil Characterization by IMS-MS and FTICR MS, 2009, American Chemical Society, Ed. 81, pp. 9941-9945.
Grizzle, P. et al., Automated Liquid Chromatographic Compound Class Group-Type Separation of Crude Oils and Bitumens Using Chemically Bonded Aminolilane, 1986, Publisher Anal. Chem., vol. 58, pp. 2389-2390.
Hasan, M.U. et al., Structural characterization of Saudi Arabian heavy crude oil by n.m.r. spectroscopy, Fuel, vol. 62, 1983, pp. 518-523.
Hidajat, K, et al., Quality characterisation of crude oils by partial least square calibration of NIR spectral profiles, Near Infrared Spectrosc, vol. 8, pp. 53-59, 2000.
Jokuty, P. et al., Hydrocarbon Groups and Their Relationships to Oil Properties and Behavior, 1995, Published by Whiticar Scientific, p. 11.
Khanmohammadi, M, et al., Characterization of petroleum-based products by infrared spectroscopyu and chemometrics, Trac Trends in Analytical Chem, vol. 35, 2012.
Kok, M, et al., High pressure TGA analysis of crude oils, Thermochimica Acta., vol. 287, No. 1, 1996, pp. 91-99.
Mckenna, Amy M., Heavy Petroleum Composition. 1. Exhaustive Compositional Analysis of Athabasca Bitumen HVGO Distillates by Fourier Transform Ion Cyclotron Resonance Mass Spectrometry: A Definitive Test of the Boduszynski Model, Energy Fuels, 24, 2010, pp. 2929-2038.
Mohammed, S., The Use of Compounds Chemically Related to Analyte as Surrogate Reference Standards in Quantitative HPLC, Feb. 2008, Produced by Kwame Nkrumah University of Science and Technology, Kumasi, p. 16.
Pande, S., et al., Cetana Number Predictions of a Trial Index Based on Compositional Analysis, American Chemical Society, 1989, pp. 308-312.
Patra, D, et al, Determination of Synchronous Fluorescence Scan Parameters for Certain Petroleum Products, Journal of Scientific & Industrial Research, Apr. 1, 2000, pp. 300-305.
Pavlovic K., Oil & Gas Journal, Nov. 22, 1999, pp. 51-56 (printed Jul. 9, 2014 from http://www.ogj.com/articles/print/volume-97/issue-47/in-this-issue/refining/gravity-and-sulfur-based-crude-valuations-more-accurate-than-believed.html).
Pereira,Thieres M. C., An evaluation of the aromaticity of asphaltenes using atmospheric pressure photoionization Fourier transform ion cyclotron resonance mass spectrometry—APP (±) FT-ICR MS, Fuel, 2014, vol. 118, 2014, pp. 348-357.
Rodgers, R. et al., Advanced Characterization of Petroleum Crude and Products by High Field Fourier Transform Ion Cyclotron Resonance Mass Spectrometry, 2002, Fuel Chemistry Division, Ed. 47(2), pp. 636-637.
Shea, T.M., Modeling Base Oil Properties using NMR Spectroscopy and Neural Networks, Tribology Transactions, vol. 46, No. 3, 2003, pp. 296-302.
Souza, C. et al., Cetane Number Assessment in Diesel Fuel by 1H or Hydrogen Nuclear Magnetic Resonance-Based Multivariate Calibration, Energy & Fuels, vol. 28, 2014, pp. 4958-4962.
Speight, Handbook of Petroleum Product Analysis, 2002.
Terra, L. et al., Petroleomics by electrospray ionization FT-ICR mass spectrometry coupled to partial least squares with variable selection methods: prediction of the total acid number of crude oils, 2014, Analyst, vol. 139, 2014, pp. 4908-4916.
University of Oldenburg, Institute of Physics, Catalogue of Optical Spectra of Oils, Jan. 2005, retrieved from http://las.physik.uni-oldenburg.de/data/spectra/indez.htm, 6 pages.
Yamashita, G.T., Evaluation of Integration Procedures for PNA Analysis by C-13 NMR, Symposium on Analytical Chemistry of Heavy Oils/Resids Presented Before the Division of Petroleum Chemistry, Inc., American Chemical Society, Dallas Meeting, Apr. 9-14, 1989, pp. 301-305.
PCT/US2016/012147, International Search Report and Written Opinion dated Jun. 1, 2016, 17 pages.

\* cited by examiner

CHARACTERIZATION OF CRUDE OIL BY FOURIER TRANSFORM ION CYCLOTRON RESONANCE MASS SPECTROMETRY

RELATED APPLICATIONS

This application Continuation-in-Part of
U.S. patent application Ser. No. 13/467,693 filed May 9, 2012, claiming priority from U.S. Provisional Patent Application No. 61/502,385 filed Jun. 29, 2011; and PCT/US2016/012147 filed Jan. 5, 2016, claiming priority from U.S. Provisional Patent Application No. 62/099,743 filed Jan. 5, 2015,
the disclosures of which are hereby incorporated by reference in their entireties.

FIELD OF THE INVENTION

This invention relates to a method and process for the evaluation of samples of crude oil and its fractions by Fourier transform ion cyclotron resonance mass spectrometry (FT-ICR MS).

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, ° C. |
|---|---|
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light Gas Oil | 205-260 |
| Mid Gas Oil | 260-315 |
| Heavy Gas Oil | 315-370 |
| Light Vacuum Gas Oil | 370-430 |
| Mid Vacuum Gas Oil | 430-480 |
| Heavy Vacuum Gas Oil | 480-565 |
| Vacuum Residue | 565+ |

The yields, composition, physical and indicative properties of these crude oil fractions, where applicable, are then determined during the crude assay work-up calculations. Typical compositional and property information obtained from a crude oil assay is given in Table 2.

TABLE 2

| Property | Unit | Property Type | Fraction |
|---|---|---|---|
| Yield Weight and Volume % | W % | Yield | All |
| API Gravity | ° | Physical | All |
| Viscosity Kinematic @ 38° C. | ° | Physical | Fraction boiling >250° C. |
| Refractive Index @ 20° C. | Unitless | Physical | Fraction boiling <400° C. |
| Sulfur | W % | Composition | All |
| Mercaptan Sulfur, W % | W % | Composition | Fraction boiling <250° C. |
| Nickel | ppmw | Composition | Fraction boiling >400° C. |
| Nitrogen | ppmw | Composition | All |
| Flash Point, COC | ° C. | Indicative | All |
| Cloud Point | ° C. | Indicative | Fraction boiling >250° C. |
| Pour Point, (Upper) | ° C. | Indicative | Fraction boiling >250° C. |
| Freezing Point | ° C. | Indicative | Fraction boiling >250° C. |
| Microcarbon Residue | W % | Indicative | Fraction boiling >300° C. |
| Smoke Point, mm | mm | Indicative | Fraction boiling between 150-250 |
| Octane Number | Unitless | Indicative | Fraction boiling <250° C. |
| Cetane Index | Unitless | Indicative | Fraction boiling between 150-400 |
| Aniline Point | ° C. | Indicative | Fraction boiling <520° C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36°–180° C.), kerosene (180°–240° C.), gas oil (240°–370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370°–520° C., and vacuum residue, comprising hydrocarbons boiling above 520° C. Crude assay data is conventionally obtained from individual analysis of these cuts to help refiners to understand the general composition of the crude oil fractions and properties so that the fractions can be processed most efficiently and effectively in an appropriate refining unit. Indicative properties are used to determine the engine/fuel performance or usability or flow characteristic or composition. A summary of the indicative properties and their determination methods with description is given below.

The cetane number of diesel fuel oil, determined by the ASTM D613 method, provides a measure of the ignition quality of diesel fuel; as determined in a standard single cylinder test engine; which measures ignition delay compared to primary reference fuels. The higher the cetane number; the easier the high-speed; direct-injection engine will start; and the less white smoking and diesel knock after start-up. The cetane number of a diesel fuel oil is determined by comparing its combustion characteristics in a test engine with those for blends of reference fuels of known cetane number under standard operating conditions. This is accomplished using the bracketing hand wheel procedure which varies the compression ratio (hand wheel reading) for the sample and each of the two bracketing reference fuels to obtain a specific ignition delay, thus permitting interpolation of cetane number in terms of hand wheel reading.

The octane number, determined by the ASTM D2699 or D2700 methods, is a measure of a fuel's ability to prevent detonation in a spark ignition engine. Measured in a standard single-cylinder; variable-compression-ratio engine by comparison with primary reference fuels. Under mild conditions, the engine measures research octane number (RON), while under severe conditions, the engine measures motor octane number (MON). Where the law requires posting of octane numbers on dispensing pumps, the antiknock index (AKI) is used. This is the arithmetic average of RON and MON, (R+M)/2. It approximates the road octane number, which is a measure of how an average car responds to the fuel.

The cloud point, determined by the ASTM D2500 method, is the temperature at which a cloud of wax crystals appears when a lubricant or distillate fuel is cooled under standard conditions. Cloud point indicates the tendency of the material to plug filters or small orifices under cold weather conditions. The specimen is cooled at a specified rate and examined periodically. The temperature at which cloud is first observed at the bottom of the test jar is recorded as the cloud point. This test method covers only petroleum products and biodiesel fuels that are transparent in 40 mm thick layers, and with a cloud point below 49° C.

The pour point of petroleum products, determined by the ASTM D97 method, is an indicator of the ability of oil or distillate fuel to flow at cold operating temperatures. It is the lowest temperature at which the fluid will flow when cooled under prescribed conditions. After preliminary heating, the sample is cooled at a specified rate and examined at intervals of 3° C. for flow characteristics. The lowest temperature at which movement of the specimen is observed is recorded as the pour point.

The aniline point, determined by the ASTM D611 method, is the lowest temperature at which equal volumes of aniline and hydrocarbon fuel or lubricant base stock are completely miscible. A measure of the aromatic content of a hydrocarbon blend is used to predict the solvency of a base stock or the cetane number of a distillate fuel. Specified volumes of aniline and sample, or aniline and sample plus n-heptane, are placed in a tube and mixed mechanically. The mixture is heated at a controlled rate until the two phases become miscible. The mixture is then cooled at a controlled rate and the temperature at which two separate phases are again formed is recorded as the aniline point or mixed aniline point.

To determine these properties of gas oil or naphtha fractions conventionally, these fractions have to be distilled from the crude oil and then measured/identified using various analytical methods that are laborious, costly and time-consuming.

Fourier transform ion cyclotron resonance mass spectrometry (FT-ICR MS) includes two components: an ionization source and a mass analyzer. The ionization source ionizes molecules, while the mass analyzer determines the mass-to-charge ratio (m/z) of ions.

New rapid and direct methods to help better understand the crude oil composition and properties from the analysis of whole crude oil will save producers, marketers, refiners and/or other crude oil users substantial expense, effort and time. Therefore, a need exists for an improved system and method for determining indicative properties of crude oil fractions from different sources.

SUMMARY OF THE INVENTION

Systems and methods for determining the indicative properties of a hydrocarbon sample are provided. In accordance with the invention, indicative properties (i.e., cetane number, pour point, cloud point and aniline point of gas oil fraction and octane number of gasoline fraction in crude oils) are predicted by density and FT-ICR MS measurement of crude oils. The correlations also provide information about the gas oil properties without fractionation/distillation (crude oil assays) and will help producers, refiners, and marketers to benchmark the oil quality and, as a result, valuate the oils without performing the customary extensive and time-consuming crude oil assays.

BRIEF DESCRIPTION OF THE DRAWINGS

Further advantages and features of the present invention will become apparent from the following detailed description of the invention when considered with reference to the accompanying drawings in which.

DETAILED DESCRIPTION OF INVENTION

Figure 1:
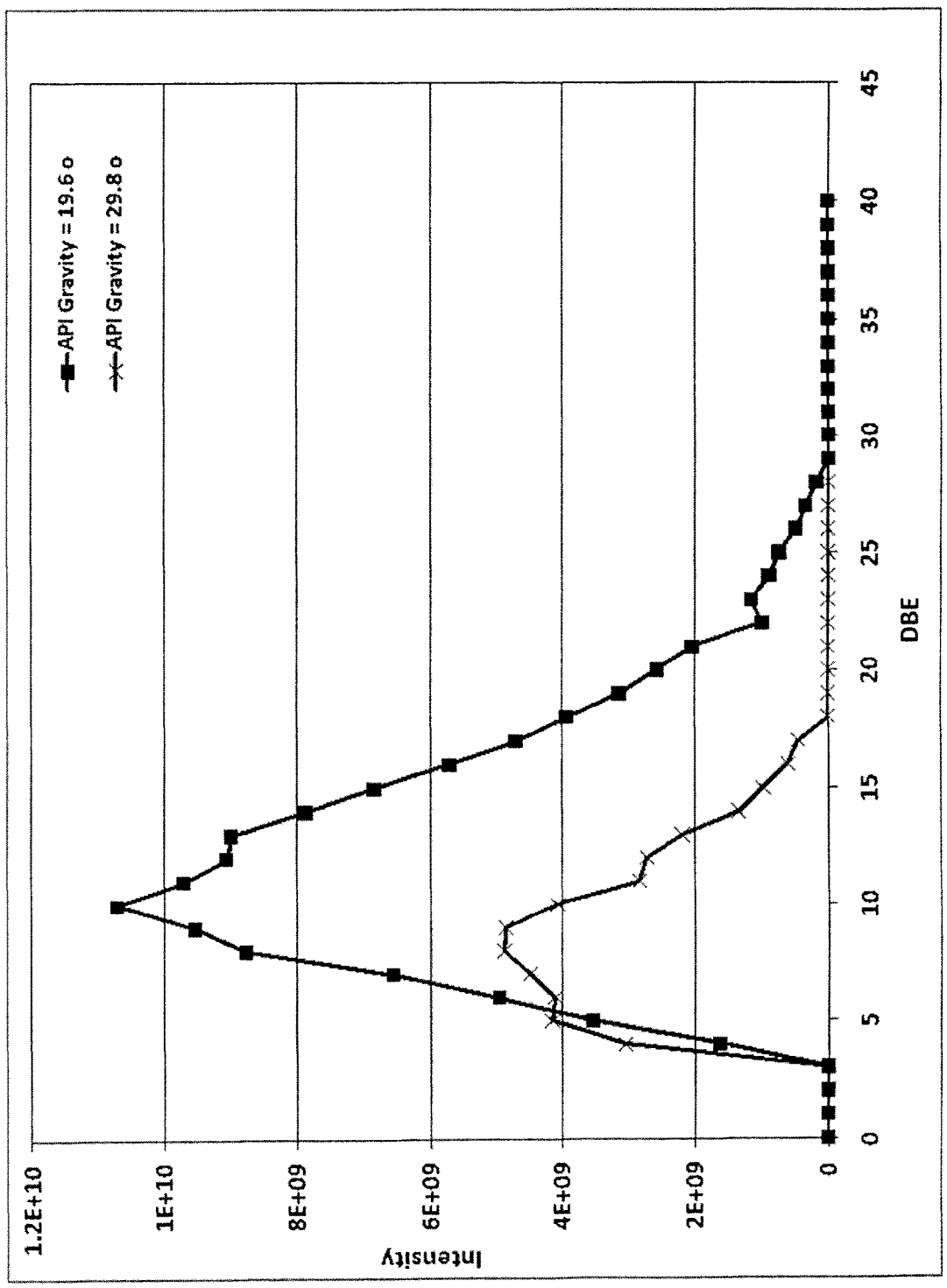
FIG. 1 is a graphic plot of typical FT-ICR MS data for two types of a crude oil sample solution prepared as described below.

A system and method is provided for determining one or more indicative properties of a hydrocarbon sample. Indicative properties (e.g., one or more of cetane number, pour point, cloud point and aniline point) of a gas oil fraction in crude oil samples are assigned as a function of FT-ICR MS measurement of a crude oil sample and the density of the crude oil sample.

The correlations provide information about gas oil and/or naphtha indicative properties without fractionation/distillation (crude oil assays) and will help producers, refiners, and marketers to benchmark the oil quality and, as a result, valuate the oils without performing the customary extensive and time-consuming crude oil assays. The currently used crude oil assay method is costly in terms of money and time. It costs about $50,000 US and takes two months to complete one assay. With the method and system herein, the crude oil can be classified as a function of FT-ICR MS measurement data, and thus decisions can be made for purchasing and/or processing.

The systems and methods are applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction. Samples can be obtained from various sources, including an oil well, stabilizer, extractor, or distillation tower.

In the system and method herein, a mass spectra is obtained by a suitable known or to be developed FT-ICR MS, and from this spectra signal intensity data is obtained (Y-axis in FIG. 1) as a function of the m/z of ions; the m/z data can be correlated to double bond equivalent (DBE) values, and carbon numbers are calculated for each identified elemental composition.

Fourier transform ion cyclotron resonance mass spectrometry (FT-ICR MS) includes two components: an ionization source and a mass analyzer. The ionization source ionizes molecules, while the mass analyzer determines the mass-to-charge ratio (m/z) of ions.

A number of ionization sources have been used in FT-ICR MS, with some being preferable for gases, others for liquids, and others for solids. Ionization sources for FT-ICR MS include electron ionization (EI), which uses a glowing filament, which may break down the molecules under study. Inductively coupled plasma ionization (ICP) is a destructive technique which applies heat to reduce a sample to its atomic components. Chemical ionization (CI), a subset of EI, adds gases such as methane, isobutane, or ammonia, producing results that are less damaging to the molecules under study. Direct analysis in real time (DART) ionizes samples at atmospheric pressure using an electron beam. Matrix-assisted, laser desorption ionization (MALDI) is a solid phase process that uses laser energy to ionize molecules off a metal target plate. Electrospray ionization (ESI), is a liquid phase process that produces a fine mist of droplets, as from an atomizer.

FT-ICR MS frequently relies on ESI or on a related variant, such as atmospheric pressure chemical ionization (APCI) or atmospheric pressure photoionization (APPI). APCI uses a corona discharge from an electrified needle to induce ionization of a solvent, which in turn reacts with the sample molecules to induce a chemical reaction resulting in an ionized sample molecule. APPI uses a photon discharge from high-intensity ultraviolet light to ionize the solvent gas, which in turn ionizes the sample molecules. APCI works well with relatively small, neutral, or hydrophobic compounds, such as steroids, lipids, and non-polar drugs. APPI works well with highly non-polar molecules like napthols and anthracenes.

Thus, in the petroleum industry, FT-ICR is conducted using ESI, and preferably the APPI variant of ESI. A petroleum sample is diluted in an appropriate solvent and infused into the spectrometer. The liquid sample is evaporated and the components are ionized by ESI or APPI, yielding unfragmented gas phase ions of the sample components. These ions are trapped in the strong magnetic field of the mass analyzer, where their mass-to-charge ratios are determined with high resolution and accuracy. The spectrometer provides a resolution of R>300,000 at m/z 400, which is high enough for routinely separating signals spaced as closely as 3.4 mDa ($SH_4$ vs. $^{12}C_3$), which is essential for the correct assignment of the elemental composition ($C_cH_hN_nO_oS_sNi_iV_v$) corresponding to each mass signal in petroleum samples. The identified elemental compositions are then classified according to the heteroatoms in their elemental composition, e.g., pure hydrocarbons, mono-sulfur (or mono-nitrogen) species for molecules with one sulfur (or nitrogen) atom, or molecules with any combination of heteroatoms. The corresponding double bond equivalent (DBE) values and carbon numbers are calculated for each identified elemental composition, where the DBE is defined as half the number of hydrogen atoms lacking from a completely saturated molecule with an otherwise identical number of carbon and heteroatoms.

Figure 2:
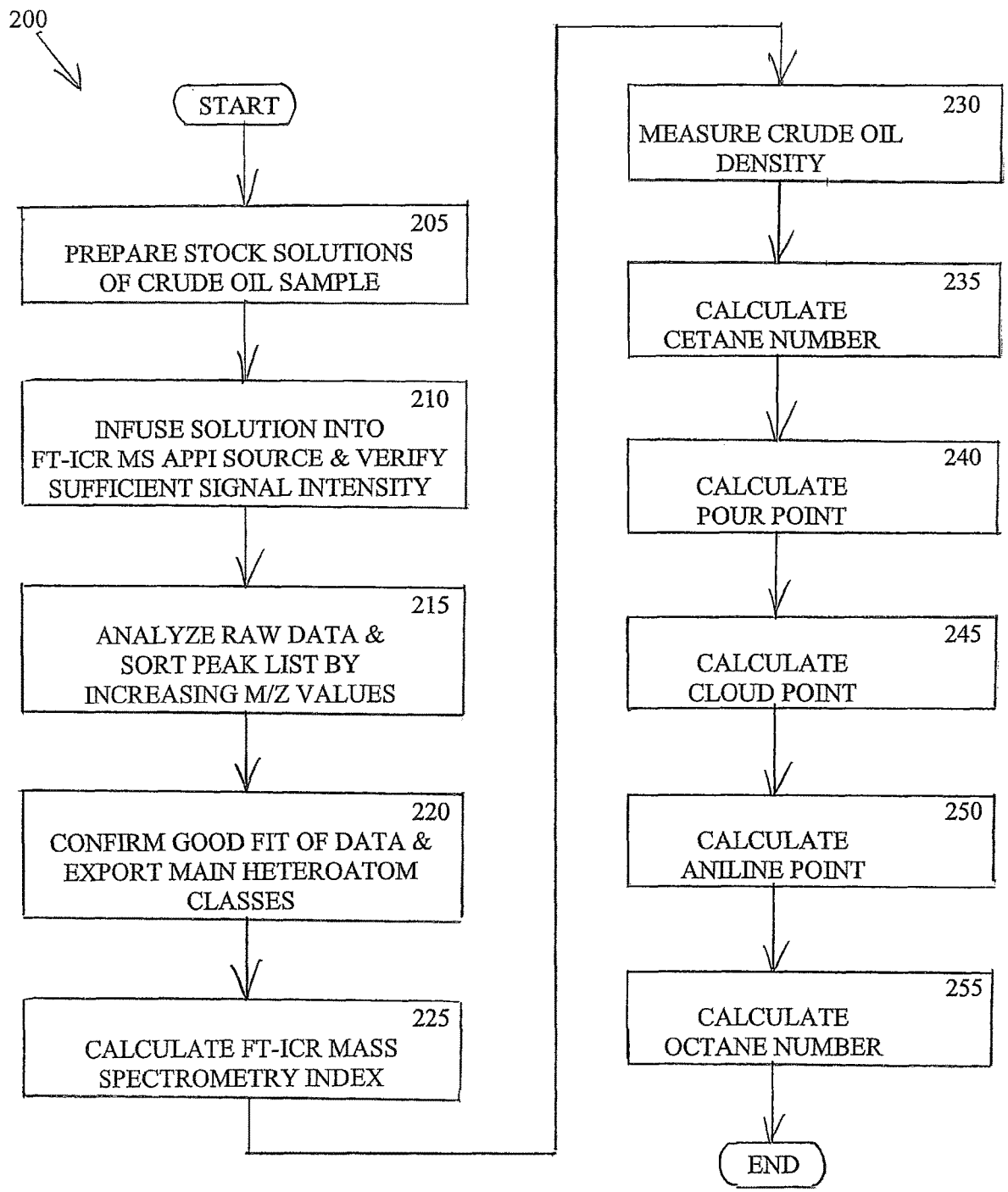
FIG. 2 is a block diagram of a method in which an embodiment herein is implemented.

FIG. 2 shows a process flowchart in a method 200 according to one embodiment herein. Solutions of crude oil samples are prepared, step 205. The prepared solutions are infused into an FT-ICR MS, using atmospheric pressure photo ionization (APPI), step 210. The raw data from step 210 is analyzed, and the resulting peak list is sorted by increasing m/z values, step 215. At step 220, the data from step 215 is confirmed to be a good fit, and main heteroatom classes are exported. In step 225, an FT-ICR MS Index is calculated and assigned. In step 230, the density of the crude oil sample is measured. In steps 235, 240, 245, 250, 255, the cetane number, the pour point, the cloud point, the aniline point and the octane number are each calculated. While FIG. 2 shows steps 235 through 255 performed sequentially, they can be performed in any order, and in certain embodiments fewer than all can be calculated and assigned.

Equation (1) shows the FT-ICR mass spectrometry index, FTMSI, which is calculated in step 225:

$$FTMSI = \sum_{DBE=min}^{max} (\text{Intensity})/(1E+11) \tag{1}$$

where:

Intensity=the intensity for each double bond equivalent (DBE).

The indicative properties (e.g., the cetane number, pour point, cloud point and aniline point of the gas oil fraction boiling in the range 180-370° C. and octane number for gasoline fraction boiling in the range 36-180° C.) of the crude oil can be predicted from the density of whole crude oil (which is determined in step 230), and from the Fourier Transform Ion Cyclotron Resonance Mass Spectrometry index (FTMSI) of crude oil (which was determined in step 225). That is, $$\text{Indicative Property}=f(\text{density}_{crude\ oil}, \text{FTMSI}_{crude\ oil}) \tag{2}$$

Equations (3) through (6) show, respectively, the cetane number, pour point, cloud point aniline point of gas oils boiling in the range 180-370° C., and equation (7) shows the octane number of gasoline boiling in the range 36-180° C. that can be predicted from the density and Fourier transform ion cyclotron resonance mass spectrometry index of crude oils. Thus, in step 235, the cetane number is calculated as:

$$\text{Cetane Number (CET)} = K_{CET} + X1_{CET} * \text{DEN} + X2_{CET} * \text{FTMSI} + X3_{CET} * \text{FTMSI}^2 + X4_{CET} * \text{FTMSI}^3 \quad (3);$$

In step 240, the pour point is calculated as:

$$\text{Pour Point (PPT)} = K_{PPT} + X1_{PPT} * \text{DEN} + X2_{PPT} * \text{FTMSI} + X3_{PPT} * \text{FTMSI}^2 X4_{PPT} * \text{FTMSI}^3 \quad (4)$$

In step 245, the cloud point is calculated as:

$$\text{Cloud Point (CPT)} = K_{CPT} + X1_{CPT} * \text{DEN} + X2_{CPT} * \text{FTMSI} + X3_{CPT} * \text{FTMSI}^2 + X4_{CPT} * \text{FTMSI}^3 \quad (5)$$

In step 250, the aniline point is calculated as:

$$\text{Aniline Point (AP)} = K_{AP} + X1_{AP} * \text{DEN} + X2_{AP} * \text{FTMSI} + X3_{AP} * \text{FTMSI}^2 X4_{AP} * \text{FTMSI}^3 \quad (6)$$

In step 255, the octane number is calculated as:

$$\text{Octane Number (ON)} = K_{ON} + X1_{ON} * \text{DEN} + X2_{ON} * \text{FTMSI} + X3_{ON} * \text{FTMSI}^2 \quad (7)$$

where:
DEN=density of the crude oil sample;
FTMSI=Fourier transform ion cyclotron resonance mass spectrometry index (derived from FT-ICR MS data); and $K_{CET}$, $X1_{CET}$–$X4_{CET}$, $K_{PPT}$, $X1_{PPT}$–$X4_{PPT}$, $K_{CPT}$, $X1_{CPT}$–$X4_{CPT}$, $K_{AP}$, $X1_{AP}$–$X4_{AP}$, $K_{ON}$, $X1_{ON}$–$X3_{ON}$ are constants that were developed using linear regression analysis of hydrocarbon data from the APPI mode of FT-ICR MS.

Figure 3:
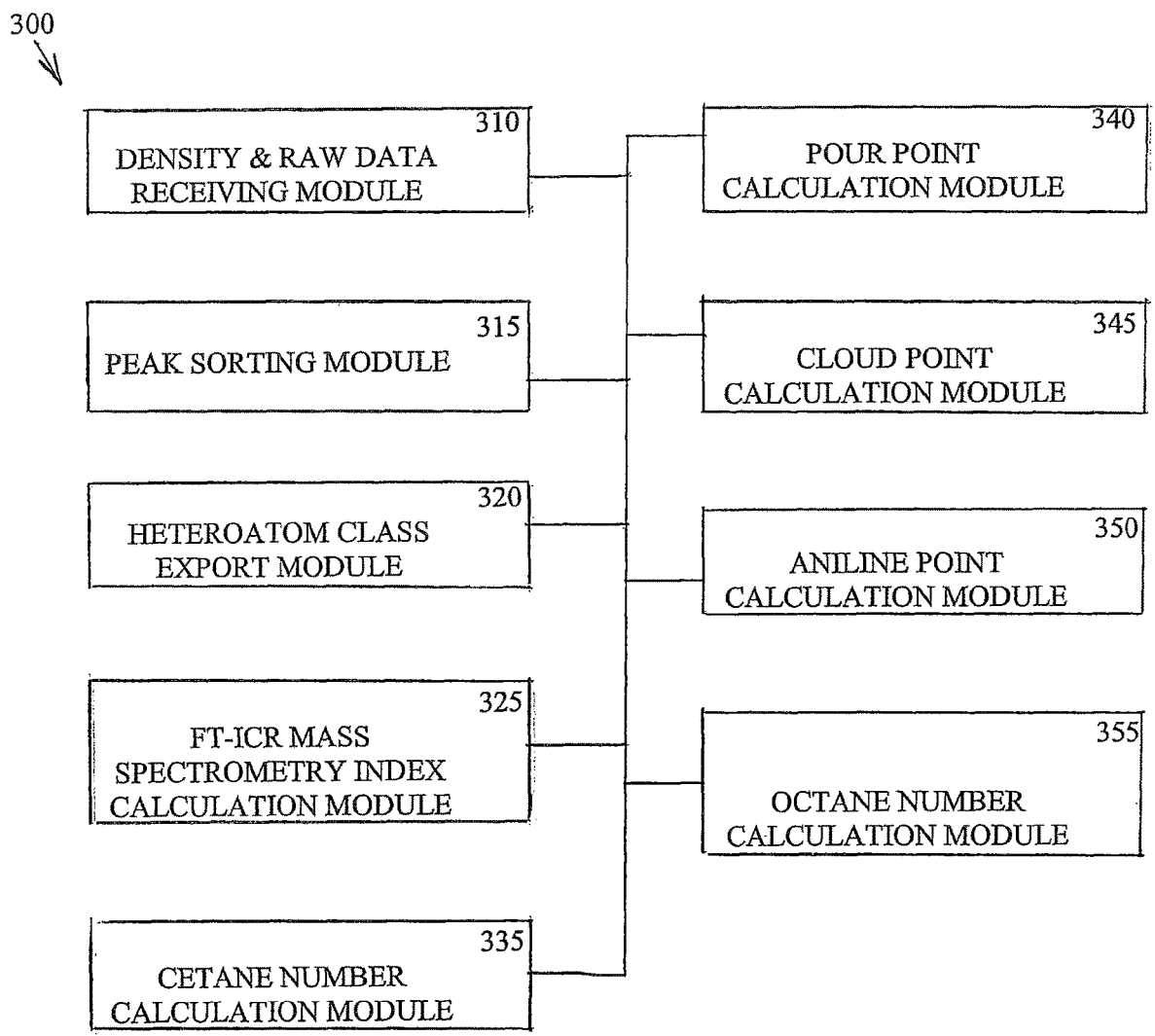
FIG. 3 is a schematic block diagram of modules of an embodiment of herein.

FIG. 3 illustrates a schematic block diagram of modules in accordance with an embodiment of the present invention, system 300. Density and raw data receiving module 310 receives Fourier transform ion cyclotron resonance mass spectrometry (FT-ICR MS) data derived from the corresponding crude oil and the density of a sample of crude oil. Peak sorting module 315 sorts the peaks by increasing m/z values. Heteroatom class export module 320 confirms a good fit of the FT-ICR MS data and uses the data to calculate the carbon numbers, double bond equivalents and intensities of the gas oil fraction. Module 330 calculates the FT-ICR mass spectrometry index (FTMSI). Cetane number calculation module 335 derives the cetane number for the gas oil fraction as a function of the FT-ICR MS peak intensity and density of the sample. Pour point calculation module 340 derives the pour point for the gas oil fraction as a function of the FT-ICR MS peak intensity and density of the sample. Cloud point calculation module 345 derives the cloud point for the gas oil fraction as a function of the FT-ICR MS peak intensity and density of the sample. Aniline point calculation module 350 derives the aniline point for the gas oil fraction as a function of the FT-ICR MS peak intensity and density of the sample. Octane number calculation module 355 derives the octane number for the gasoline fraction as a function of the FT-ICR MS peak intensity and density of the sample.

Figure 4:
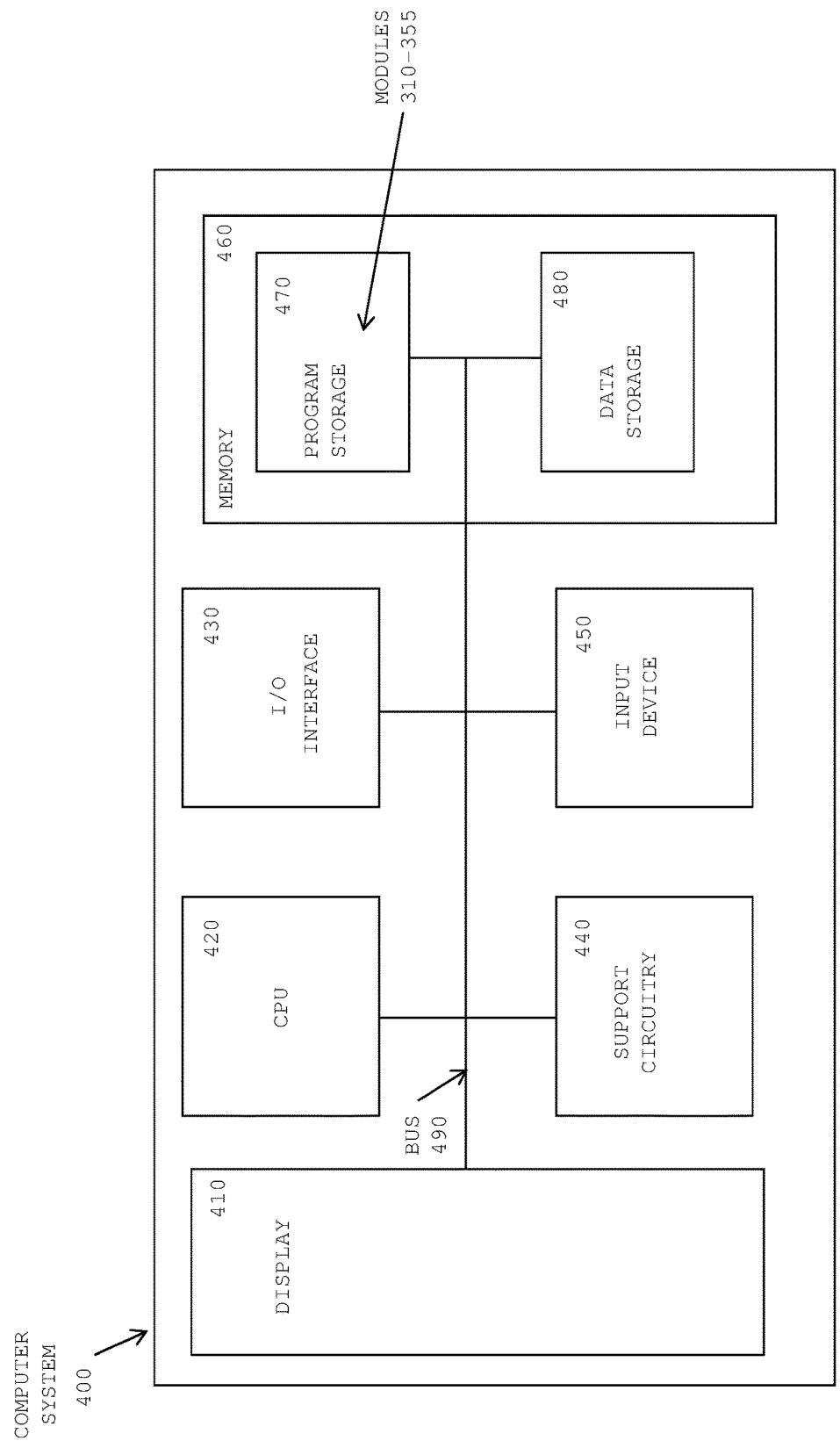
FIG. 4 is a block diagram of a computer system in which an embodiment herein is implemented.

FIG. 4 shows an exemplary block diagram of a computer system 400 by which the herein calculation modules can be implemented is shown in FIG. 4. Computer system 400 includes a processor 420, such as a central processing unit, an input/output interface 430 and support circuitry 440. In certain embodiments, where the computer system 400 requires a direct human interface, a display 410 and an input device 450 such as a keyboard, mouse or pointer are also provided. The display 410, input device 450, processor 420, and support circuitry 440 are shown connected to a bus 490 which also connects to a memory 460. Memory 460 includes program storage memory 470 and data storage memory 480.

Note that while computer system 400 is depicted with direct human interface components display 410 and input device 450, programming of modules and exportation of data can alternatively be accomplished over the input/output interface 430, for instance, where the computer system 400 is connected to a network and the programming and display operations occur on another associated computer, or via a detachable input device as is known with respect to interfacing programmable logic controllers.

Program storage memory 470 and data storage memory 480 can each comprise volatile (RAM) and non-volatile (ROM) memory units and can also comprise hard disk and backup storage capacity, and both program storage memory 470 and data storage memory 480 can be embodied in a single memory device or separated in plural memory devices. Program storage memory 470 stores software program modules and associated data, and in particular stores a density and raw data receiving module 310, peak sorting module 315, heteroatom class export module 320, FTMSI calculation module 325, cetane number calculation module 330, pour point calculation module 340, cloud point calculation module 345, aniline point calculation module 350, and octane number calculation module 355. Data storage memory 480 stores data used and/or generated by the one or more modules of the present invention, including but not limited to density of the crude oil sample, raw data generated by the FT-ICR MS APPI source, and m/z correlations with DBE data and carbon number data.

The calculated and assigned results in accordance with the systems and methods herein are displayed, audibly outputted, printed, and/or stored to memory for use as described herein.

It is to be appreciated that the computer system 400 can be any general or special purpose computer such as a personal computer, minicomputer, workstation, mainframe, a dedicated controller such as a programmable logic controller, or a combination thereof. While the computer system 400 is shown, for illustration purposes, as a single computer unit, the system can comprise a group/farm of computers which can be scaled depending on the processing load and database size, e.g., the total number of samples that are processed and results maintained on the system. The computer system 400 can serve as a common multi-tasking computer.

Computer system 400 preferably supports an operating system, for example stored in program storage memory 470 and executed by the processor 420 from volatile memory. According to the present system and method, the operating system contains instructions for interfacing the device 400 to the calculation module(s). According to an embodiment of the invention, the operating system contains instructions for interfacing computer system 400 to the Internet and/or to private networks.

Example

Crude oil samples were prepared and analyzed by atmospheric pressure photo ionization (APPI) Fourier transform ion cyclotron resonance mass spectrometry (FT-ICR MS) according to the method 200 described herein, and illustrated in FIG. 2.

In step 205, Stock solution 1 is prepared by dissolving a 100 μL sample of the crude oil in 10 mL of toluene (or alternatively, in a 50/50% volume mixture of toluene with methanol, methylene chloride, dichloromethane or tetrahydrofuran). If complete solubility is not attained, based upon visual observation against a light source, methylene chloride is added to achieve a clear solution. The solution is shaken for a minimum of 20 seconds.

Solution 2 is prepared with a 1:100 dilution of solution 1 in methylene chloride. The miscibility of the solvent mix must be ensured.

Solution 3 is prepared with a 1:10 dilution of solution 2 in methylene chloride (i.e., 100 µL of solution 2 in 900 µL solvent).

The dilution ratio depends on the sample and has to be determined empirically on a case-by-case basis, starting from solution 3, then advancing to solution 2 and then to solution 1.

Key Instrument Parameters

For each analysis of a sample, the operator tunes the spectrometer settings to optimize performance. Key parameters and default settings follow:

TD (Fid Size): 4M
Average Spectra: 100
Source Accumulation: 0.001 s
Ion Accumulation Time: 0.001 s
TOF (AQS): variable, depending on sample
APPI Temperature 250-400° C., depending on sample
Detection Mode: Broadband
Low Mass: 150 to 350 m/z
High Mass: 3000 m/z Mass Calibration and Performance Check The performance of the FT-ICR MS instrument is checked by obtaining a mass calibration in ESI positive mode. This ESI calibration can be used in the APPI mode by exchanging the ESI ion source with the APPI source. The mass calibration remains valid for one day of normal operation as long as the key instrument parameters described above have not been changed. A change of any of the key instrument parameters requires a complete recalibration by switching to the ESI source, calibration, followed by switching back to the APPI source.

Analysis

In step 210, the analysis begins with Solution 3, which is directly infused into the mass calibrated FT-ICR MS APPI source by a syringe pump. The operator records and averages 100 accumulated scans, which serve as a general basis for fine-tuning the instrument parameters.

If sufficient signal intensity ($10^8$ to $10^9$ units) is not obtained with Solution 3, the analysis is repeated with Solution 2. If the analysis with Solution 2 still does not yield sufficient signal intensity, the analysis is repeated with Solution 1.

The operator checks the signal shape at the beginning, middle and end of the mass range. An excessive sample load can be diagnosed by a signal splitting. In case of signal splitting, all signals will appear as two closely aligned signals or, in severe cases, even as a group of signals. When the operator observes such signal splitting, he should dilute the sample until he obtains a good independent signal shape.

The following pass/fail criteria are applied to the tests. A mass calibration is acceptable when every mass calibrant in the mass range of the sample does not deviate more than ±0.2 ppm from the expected value, except calibrants that are discarded from the list due to either low intensity (below 3 times the baseline noise) or a calibrant signal that is overlapping a contamination signal.

Data Processing Workflow

Data processing is an extensive exercise involving four different software packages as described below. Data processing can significantly impact the quality of the produced data and therefore must be performed by, or under the direction of an experienced scientist. The trade names of the respective programs are followed by their sources.

DataAcquisition from Bruker Daltonics of Bremen, Germany. The raw data is checked for sufficient signal shape and intensity as described above and, if necessary, re-measured until sufficient signal shape and intensity are obtained.

DataAnalysis from Bruker Daltonics of Bremen, Germany. The recorded raw data file is loaded into the DataAnalysis software. In step 215, the peak list is sorted according to increasing m/z values. The m/z values and intensities are then saved as a peak list "text file."

Composer from SierraAnalytics of Modesto, California. The peak lists are loaded into the Composer software. The Composer software is started and a suitable parameter file is loaded. In step 220, the recalibration is checked by looking at the identified species. The individual series are inspected for consistency, i.e., for missing series and/or interrupted series, which may indicate non-ideal re-calibration. In exceptional cases, recalibration parameters have to be fine tuned until a good fit of the data is obtained. The main heteroatom classes, which are those constituting more than 1 percent of the assigned heteroatom classes, are exported into the Microsoft Excel spreadsheet "Automatic Processing Composer Data.xls."

Excel Spreadsheet Automatic Processing Composer Data: This in-house developed spreadsheet processes the elemental compositions calculated by the Composer software and produces all graphs in a final reporting form. An Excel workbook with one summary tab and detail tabs for each identified heteroatom class is created.

Exemplary constants $K_{CET}$, $X1_{CET}$-$X4_{CET}$, $K_{PPT}$, $X1_{PPT}$-$X4_{PPT}$, $K_{CPT}$, $X1_{CPT}$-$X4_{CPT}$, $K_{AP}$, $X1_{AP}$-$X4_{AP}$, $K_{ON}$, $X1_{ON}$-$X3_{ON}$ are were developed using linear regression analysis of hydrocarbon data from the APPI mode of FT-ICR MS, and are given in Table 3.

TABLE 3

| Constants | Cetane Number | Pour Point | Cloud Point | Aniline Point | Octane Number |
|---|---|---|---|---|---|
| K | −322.2 | −266.1 | 4.5 | 166.7 | 128.8 |
| X1 | 419.0 | 299.4 | −3.4 | −119.8 | −91.1 |
| X2 | −22.9 | −180.7 | −127.2 | 51.0 | 8.8 |
| X3 | 198.8 | 558.1 | 330.6 | −123.9 | 3.2 |
| X4 | −175.3 | −387.4 | −215.0 | 70.2 | — |

A sample of Arabian medium crude with a 15° C./4° C. density of 0.8828 Kg/l was analyzed by APPI FT-ICR MS, using the described method. The mass spectral data is presented in Table 4 and is shown in FIG. 1 as the sample with an API gravity of 29.80.

The FT-ICR MS index, FTMSI, is calculated using equation (1) by summing the intensities of the detected peaks and then dividing by 1E+11, with the value in the example calculated as 0.40707.

TABLE 4

| Double Bond Equivalent (DBE) | Intensity |
|---|---|
| 0 | 0 |
| 1 | 0 |
| 2 | 0 |
| 3 | 0 |
| 4 | 3047754803 |
| 5 | 4148548475 |
| 6 | 4106580447 |
| 7 | 4475073884 |

TABLE 4-continued

| Double Bond Equivalent (DBE) | Intensity |
| --- | --- |
| 8 | 4874039296 |
| 9 | 4852787148 |
| 10 | 4060232629 |
| 11 | 2831278701 |
| 12 | 2726027390 |
| 13 | 2196336212 |
| 14 | 1348225844 |
| 15 | 980497462 |
| 16 | 604773496 |
| 17 | 455374155 |
| 18 | 0 |
| 19 | 0 |

Applying equation (3) and the constants from Table 3, $$\text{Cetane Number } (CET) = K_{CET} + X1_{CET} * DEN + X2_{CET} * FTMSI +$$
$$X3_{CET} * FTMSI^2 + X4_{CET} * FTMSI^3$$
$$= (-322.2) + (419.0)(0.8828) + (-22.9)(0.40707) +$$
$$(198.8)(0.40707)^2 + (-175.3)(0.40707)^3$$
$$= 59$$

Applying equation (4) and the constants from Table 3, $$\text{Pour Point } (PPT) = K_{PPT} + X1_{PPT} * DEN + X2_{PPT} * FTMSI +$$
$$X3_{PPT} * FTMSI^2 + X4_{PPT} * FTMSI^3$$
$$= (-266.1) + (299.4)(0.8828) + (-180.7)(0.40707) +$$
$$(558.1)(0.40707)^2 + (-387.4)(0.40707)^3$$
$$= -9$$

Applying equation (5) and the constants from Table 3, $$\text{Cloud Point } (CPT) = K_{CPT} + X1_{CPT} * DEN + X2_{CPT} * FTMSI +$$
$$X3_{CPT} * FTMSI^2 + X4_{CPT} * FTMSI^3$$
$$= (4.5) + (-3.4)(0.8828) + (-127.2)(0.40707) +$$
$$(330.6)(0.40707)^2 + (-215.0)(0.40707)^3$$
$$= -10$$

Applying equation (6) and the constants from Table 3, $$\text{Aniline Point } (AP) = K_{AP} + X1_{AP} * DEN + X2_{AP} * FTMSI +$$
$$X3_{AP} * FTMSI^2 + X4_{AP} * FTMSI^3$$
$$= (166.7) + (-119.8)(0.8828) + (51.0)(0.40707) +$$
$$(-123.9)(0.40707)^2 + (70.2)(0.40707)^3$$
$$= 66$$

Applying equation (7) and the constants from Table 3, $$\text{Octane Number } (ON) = K_{ON} + X1_{ON} * DEN + X2_{ON} * FTMSI +$$
$$X3_{ON} * FTMSI^2$$
$$= (128.8) + (-91.1)(0.8828) +$$
$$(8.8)(0.40707) + (3.2)(0.40707)^2$$
$$= 52$$

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to In re Beauregard, 35 USPQ2d 1383 (U.S. Pat. No. 5,710,578), the present invention contemplates and includes this type of computer readable media within the scope of the invention. In certain embodiments, pursuant to In re Nuijten, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached figure; however, modifications will be apparent to those of ordinary skill in the art and the scope of protection for the invention is to be defined by the claims that follow.

We claim:

1. A method for operating a computer to assign an indicative property to a gas oil fraction or a gasoline fraction of an oil sample, wherein the oil sample is selected from the group consisting of crude oils, bitumens, heavy oils and shale oils, the method comprising:
   deriving from the oil sample Fourier transform ion cyclotron resonance mass spectrometry (FT-ICR MS) data from a Fourier transform ion cyclotron resonance mass spectrometer (FT-ICR MS), the FT-ICR MS data indicative of intensities at corresponding double bond equivalents (DBE);
   obtaining a density of the oil sample;
   entering into the computer the density of the oil sample and the FT-ICR MS data;

calculating an FT-ICR MS index (FTMSI) as $$FTMSI = \sum_{DBE=min}^{max} (\text{Intensity})/(1E+11),$$

where intensity=the intensity for each double bond equivalent (DBE); and deriving the indicative property as a function of the FTMSI and the density of the oil sample.

2. The method of claim 1 wherein the oil sample is crude oil.

3. The method of claim 1 wherein the oil sample is obtained from an oil well, stabilizer, extractor, or distillation tower.

4. The method of claim 1 wherein the indicative property is a cetane number.

5. The method of claim 1 wherein the indicative property is a pour point.

6. The method of claim 1 wherein the indicative property is a cloud point.

7. The method of claim 1 wherein the indicative property is an aniline point.

8. The method of claim 1 wherein the indicative property is an octane number.

9. The method of claim 1 wherein plural indicative properties are calculated including at least two indicative properties selected from the group consisting of cetane number, pour point, cloud point, aniline point and octane number.

10. The method of claim 1 wherein the indicative property is of a gas oil fraction boiling in the nominal range 180-370° C.

11. The method of claim 1 wherein the indicative property is of a gasoline fraction boiling in the nominal range 36-180° C.

12. The method of claim 1, wherein the FT-ICR MS covers masses that are in the range 150-1400 m/z.

13. The method of claim 1, wherein the carbon numbers detected by FT-ICR MS are in the range 1-60.

14. The method of claim 1, wherein the double bond equivalents calculated by FT-ICR MS are in the range 1-40.

* * * * *